(12) United States Patent
Gahlert et al.

(10) Patent No.: US 10,589,000 B2
(45) Date of Patent: Mar. 17, 2020

(54) BONE SUBSTITUTE MATERIAL MADE OF ZIRCONIUM DIOXIDE CERAMIC

(71) Applicants: Michael Gahlert, Munich (DE); Stefan Gahlert, Stuttgart (DE)

(72) Inventors: Michael Gahlert, Munich (DE); Stefan Gahlert, Stuttgart (DE)

( * ) Notice: Subject to any disclaimer, the term of this patent is extended or adjusted under 35 U.S.C. 154(b) by 0 days.

(21) Appl. No.: 16/209,134

(22) Filed: Dec. 4, 2018

(65) Prior Publication Data

US 2019/0105427 A1    Apr. 11, 2019

Related U.S. Application Data

(63) Continuation of application No. PCT/EP2017/063552, filed on Jun. 2, 2017.

(30) Foreign Application Priority Data

Jun. 9, 2016 (DE) .......................... 10 2016 110 622
Jun. 22, 2016 (DE) .......................... 10 2016 111 431

(51) Int. Cl.

| A61L 27/10 | (2006.01) |
| A61L 27/56 | (2006.01) |
| C04B 35/486 | (2006.01) |
| C04B 35/634 | (2006.01) |
| C04B 38/06 | (2006.01) |
| C04B 35/48 | (2006.01) |
| C04B 38/00 | (2006.01) |
| C04B 111/00 | (2006.01) |

(52) U.S. Cl.
CPC ............... *A61L 27/10* (2013.01); *A61L 27/56* (2013.01); *C04B 35/48* (2013.01); *C04B 35/486* (2013.01); *C04B 35/63436* (2013.01); *C04B 38/0054* (2013.01); *C04B 38/0058* (2013.01); *C04B 38/0615* (2013.01); *A61L 2430/02* (2013.01); *C04B 2111/00836* (2013.01); *C04B 2235/3246* (2013.01); *C04B 2235/5409* (2013.01); *C04B 2235/5436* (2013.01); *C04B 2235/604* (2013.01); *C04B 2235/6027* (2013.01); *C04B 2235/656* (2013.01); *C04B 2235/6562* (2013.01); *C04B 2235/78* (2013.01)

(58) Field of Classification Search
None
See application file for complete search history.

(56) References Cited

U.S. PATENT DOCUMENTS

| 4,309,488 | A | 1/1982 | Heide et al. |
| 10,004,668 | B2 * | 6/2018 | Brodkin ............... A61K 6/0008 |
| 2004/0043051 | A1 | 3/2004 | Pilliar et al. |
| 2005/0100578 | A1 | 5/2005 | Schmid et al. |
| 2005/0106534 | A1 * | 5/2005 | Gahlert ............... A61C 8/0012 433/173 |
| 2011/0136653 | A1 | 6/2011 | Koebel et al. |

FOREIGN PATENT DOCUMENTS

| DE | 10060036 C1 | 8/2002 |
| DE | 10258773 A1 | 7/2004 |
| EP | 0006544 A1 | 1/1980 |
| EP | 2826495 A1 | 1/2015 |

OTHER PUBLICATIONS

International Search Report and Written Opinion dated May 25, 2018 for counterpart PCT Application No. PCT/EP2017063552.

* cited by examiner

*Primary Examiner* — Celeste A Roney
(74) *Attorney, Agent, or Firm* — Shuttleworth & Ingersoll, PLC; Jason Sytsma

(57) ABSTRACT

A bone substitute material is disclosed consisting of a zirconium dioxide ceramic having preferably an open porosity. The bone substitute material can be used in particle form or in block form.

11 Claims, No Drawings

BONE SUBSTITUTE MATERIAL MADE OF ZIRCONIUM DIOXIDE CERAMIC

CROSS-REFERENCES TO RELATED APPLICATIONS

This application is a continuation of international patent application PCT/EP2017/063552, filed on Jun. 2, 2017 designating the U.S., which international patent application has been published in German language and claims priority from German patent application 10 2016 110 622.4, filed on Jun. 9, 2016 and from German patent application 10 2016 111 431.6, filed on Jun. 22, 2016. The entire contents of these priority applications is incorporated herein by reference.

BACKGROUND

The invention relates to a bone substitute material.

In dental implantology compromised anatomical bone structures are often supplemented with additional bone augmentation measures. Apart from the possibility of the body's vital bone of a donor site to the recipient site to transfer (autologous bone), there is also the possibility of a bone substitute material (BSM).

Herein a distinction is made between allogeneic, alloplastic and xenogenic BSM. Under allogeneic BSM bone from other people is understood which was prepared in the laboratory by decalcification or freeze-drying. The alloplastic BSM refers to synthetically produced BSM, such as hydroxyapatite, while xenogenic BSM is produced from bovine bone, algae or coral. Apart from the body's autologous BSM which stimulates bone formation and is called osseoinductive, all other BSMs osseoconductive. This refers to the guidance function of the BSM which shall allow ingrowth of stationary permanent jaw bone, the so-called bearing tissue.

Biocompatible BSMs are recognized in dental implantology worldwide, based on evidence and numerous studies investigated scientifically based on evidence.

Alloplastic BSMs have been known in the prior art for decades in the form of various inorganic BSMs. Usually they contain hydroylapatite and/or calcium phosphate (see for instance DE 100 60 036 C1, EP 0 006 544 A1). Partially also calcium phosphate is used which is processed into a porous ceramic, which may also be present in particle form (see DE 102 58 773 A1).

Partially into the inorganic bone substitute material, such as hydroxylapatite, also organic components are admixed, such as collagen, to improve the osseoconductivity (see for instance EP 2 826 495 A1).

Basically, in inorganic bone substitute materials always there is the problem that these synthetically produced BSMs do not stimulate bone formation itself, but can provide some guidance function for the bone formation only.

SUMMARY

According to a first aspect of the invention there is disclosed a bone substitute material on inorganic basis which is very well tolerated by the body.

According to a second aspect of the invention there is disclosed a bone substitute material on inorganic basis that has a good osseoconductivity, and that, in particular, can be used in dental practice to effect a lasting bone formation or osseointegration, respectively, within a short healing time, and which is particularly suitable for placing implants.

According to a first aspect of the invention there is disclosed a bone substitute material on inorganic basis for use in dental implantology, consisting of a zirconium dioxide ceramic configured in particulate form.

According to another aspect of the invention the bone substitute material has a particle size in the range of 0.1 mm to 6.0 mm.

Zirconium dioxide is distinguished by an excellent biocompatibility and a full allergy freedom. Even without costly additional measures, such as an admixture of artificial organic or animal additive materials a good osseoconductivity can be reached.

In a preferred embodiment of the invention the BSM is used in particulate form, preferably with a particle size in the range of 0.1 to 6 mm, further preferred in the range of 0.2 to 4 mm.

This allows for a direct use in dental implantology for allowing an individual bone formation in defect regions.

Preferably the BSM is macroporous with an open porosity.

Herein there may be macropores having a mean pore diameter in the range of 10 micrometers to 500 micrometers, preferably in the range of 50 micrometers to 300 micrometers, more preferably in the range of 60 to 250 micrometers.

By such an open porosity the osseoconductivity is significantly improved. The interconnected pores allow ingrowth of blood cells and proteins, thus allowing an improved osseointegration.

According to a further feature of the invention the BSM is microporous, preferably with an open porosity.

Here in the micropores may have an average pore diameter of less than 10 micrometers, preferably of less than 1 micrometer, preferably of at least 5 nanometers.

Such a microstructure induces a capillary action that supports a fluid intake. Also in this way an improvement of the osseoconduction is facilitated.

According to a further feature of the invention the BSM comprises a bimodal porosity with macropores and micropores.

By combining the open macro-porosity with the open micro-porosity in this way both advantageous properties can be combined. In total, a further improved osseoconduction is reached.

As far as the BSM is used in particulate form, depending from the particle size in case of very small particles, either a solid design is preferred, or in case of larger particles also a macroporous and/or microporous design, as described above.

With particle sizes from about 1 to 2 millimeters in diameter a porous design is preferred, to improve the osseointegration.

With smaller particle sizes a macro-porosity is dispensed with, for the sake of stability. However, a micro-porosity can further improve osseointegration.

In contrast, block-shaped BSM, which can be made in any form, preferably is used with an open macro-porosity and possibly also with open micro-porosity.

According to a further feature of the invention the BSM consists of a tetragonal, polycrystalline zirconium dioxide (TZP). This may be stabilized by means of Y2O3, for example by the addition of 3 wt.-% Y2O3.

With TZP maximum strength is achieved. However, basically also BSM that is partially stabilized with MgO (PSZ) is suitable.

According to a further feature of the invention the porosity is in the range of 0.1 to 90%, preferably in the range of 1 to 50%, more preferred in the range of 5 to 30%.

With such a porosity a particularly good osseoconductivity and osseointegration can be reached.

According to a further feature of the invention the BSM is used in block form, preferably macroporous with open porosity.

A use in block form allows a bone formation of larger regions. To this end preferably several prepared dimensions are kept.

Unless non-dental applications are concerned, such as in the reconstruction of various bone fractures, the BSM can also be produced in special forms, which can also be adapted specifically mated to the patient, if necessary.

According to a further feature of the invention the BSM comprises an etched surface.

The osseoinduction is further improved by an etching treatment, such as by means of hydrofluoric acid, of the outer surface and the inner surfaces as a result of the open porosity.

According to another aspect of the invention there is disclosed a method for producing a porous bone substitute material from a zirconium dioxide ceramic, wherein zirconium dioxide powder with organic additives, in particular in the form of short fibers, three-dimensional structures, for instance in the form of a woven or knitted fabric, and/or in the form of powder, preferably made of plastic, is added, preferably with the addition of binders, is shaped into a precursor body and sintered thereafter.

In this way a macroporous body with an open porosity can be produced. As the short fibers or the three-dimensional structure or the powder of organic material upon heating decompose completely, an open porosity can be produced by the gases released in this way. This is controlled in particular by the proportion of the added fibers, as well as by their diameter and length, or by the configuration of the three-dimensional structure, the particle size of the organic powder, the particle size of the zirconium dioxide powder and the used temperature program, respectively.

Herein a bimodal porosity can be generated, in that the sintering process is terminated controlled, before the normally initially present micropores can outgrow fully during sintering. Alternatively, also organic additives can be added that have a bimodal size distribution.

As far as a three-dimensional structure, such as in the form of a fabric or of a knitted fabric is used, then it can be dimensioned in a suitable manner to produce an open porosity, as homogeneous as possible, during subsequent firing. Also a generation of a textured porosity is possible.

For the preparation of a homogeneous mixture of the components a pelletizing within a pelletizing vessel is particularly suitable, that is a pelletizing on a pelletizing disc that is rotatably driven, or within a rotatably driven drum.

According to a further feature of the invention the shaping is done by pressing, preferably by uniaxial or isostatic pressing, by slip casting or by centrifugal casting, with subsequent drying, or by a different powder technological method.

Also herein preferably organic additives are added, in particular short fibers or three-dimensional structures made of plastic, having a suitable diameter and a suitable length, which decompose upon subsequent sintering, so as to produce a macroporous structure.

According to a further feature of the invention, a porous BSM is prepared from a zirconium dioxide ceramic, in that an open-porous plastic foam is submerged vented within a slurry with zirconium dioxide powder is subsequently removed from the slurry, dried and sintered.

Also in this way a macroporous BSM can be manufactured from zirconium dioxide. This method is known in connection with the preparation of porous ceramic bodies as the so-called replica method.

According to a further feature of the invention the obtained material is ground into particles after sintering.

According to a further feature of the invention the microscale zirconia powder is used with an average specific surface are in the range of 5 to 100 $m^2/g$.

According to a further feature of the invention sintering is carried out in the range of 850° C. to 1750° C., preferably in the range of 850° C. to 1550° C., more preferably in the range of 900° C. to 1350° C.

The used sintering temperature depends in particular on the powder properties of the zirconia powder, in particular on the average specific surface area, or on the mean particle size. The larger the average specific surface area, the lower usually is the sintering temperature.

With powders in the range of about 20 to 50 $m^2/g$ the sintering temperatures are usually in the range of about 1250° C. to 1350° C.

As far as a pre-sintering to a green body is done, which can be machined in the green state, to produce a certain shape and size, the pre-sintering temperature is about 100 to 500 K below the temperature of the final sintering.

EXAMPLES

Example 1

Commercially available TZP powder (stabilized with 3 wt.-% of Y2O3) with an average specific surface area of 50 $m^2/g$ is mixed with 20 wt.-% of short fibers of polyvinylchloride (PVC) having an average diameter of about 50 micrometers and an average length of 500 micrometers, while adding a binder (1 wt.-% of isopropanol), so that the short fibers are randomly distributed. Thereafter an uniaxial pressing is carried out using a suitable steel die (at a pressure of e.g. 20 to 50 bars).

Subsequently, a heating to about 1350° C. at about 50 K/min and a holding at 1350° C. for about 30 to 120 minutes is performed, thereafter cooling by switching off.

In this way there is obtained a macroporous block of TZP ceramic having an open porosity. The material thus obtained can be ground to porous particles by means of a ball mill and can be screened accordingly to a desired particle size distribution.

Instead of an uniaxial pressing, also the powder mixture can be pressed isostatically.

Example 2

For the preparation of powdered BSM, that is non-porous, commercially available zirconium dioxide is ground to the desired particle size distribution and is subsequently sieved. This is of particular interest for smaller particle sizes, such as smaller than 1 to 2 millimeters in diameter.

Example 3

The material of example 1 was not ground, but directly used in block form. It can be brought into the desired size and/or shape by a mechanical treatment using diamond tools.

Example 4

Comercially available TZP powder (stabilized with 3 wt.-% of Y2O3) with an average specific surface area of 50

$m^2/g$ is mixed with 5 wt.-% to 10 wt.-% of short fibers of polyvinylchloride (PVC) having an average diameter of about 50 micrometers and an average length of 500 micrometers, while adding a binding agent (1 wt.-% of isopropanol), and is isostatically pressed thereafter (pressure e.g. 500 to 1000 bars).

This is followed by a heating to about 900° C. at about 50 K/min and a holding for about 15 to 30 minutes, thereafter a cooling by switching off. This provides a macroporous green body which can be machined in the green state, for example by means of an automatically controlled milling device. Herein the degree of shrinkage for the subsequent sintering process is taken into account.

Finally, a final sintering is carried out at about 1300° C. (heating at about 50 K/min, thereafter holding at 1300° C. for about 15 to 60 minutes). This yields a macroporous zirconium dioxide body with open porosity.

Example 5

An open-porous plastic foam is immersed within a slurry with zirconium dioxide powder according to example 1, is impregnated with the slurry, followed by drying (60 minutes at 90° C.), followed by sintering according to example 1. This yields an open porous zirconium dioxide ceramic.

Example 6

A post treatment is performed with respect to the examples 1 to 5, by carrying out an etching treatment by immersing in hydrofluoric acid, in which the fully sintered and optionally ground BSM is immersed for example in 40% hydrofluoric acid and etched 5 to 60 minutes, preferably at elevated temperature, for example at 60 to 70° C.

What is claimed is:

1. A bone substitute material for use in dental implantology, consisting of a zirconium dioxide ceramic configured in particulate form having a particle size in the range of 0.1 mm to 6.0 mm.

2. The bone substitute material of claim 1, having a particle size in the range of 0.2 to 4.0 mm.

3. The bone substitute material of claim 1, which is macroporous with an open porosity.

4. The bone substitute material of claim 3, comprising macropores with an average pore diameter in the range of 10 micrometers to 500 micrometers.

5. The bone substitute material of claim 1, comprising micropores with an average pore diameter of less than 10 micrometers.

6. The bone substitute material of claim 5, comprising micropores having an open porosity.

7. The bone substitute material of claim 5, comprising micropores with an average pore diameter of less than 1 micrometer.

8. The bone substitute material of claim 1, having a bimodal porosity including macropores and micropores.

9. The bone substitute material of claim 1, consisting of tetragonal, polycrystalline zirconium dioxide (TZP).

10. The bone substitute material of claim 1, wherein the porosity is in the range of 1 to 50%.

11. The bone substitute material of claim 1, wherein the porosity is in the range of 5 to 30%.

* * * * *